(12) United States Patent
Grossman et al.

(10) Patent No.: US 9,476,837 B2
(45) Date of Patent: Oct. 25, 2016

(54) METHOD AND SYSTEM FOR IMPROVING OPTICAL MEASUREMENTS ON SMALL TARGETS

(71) Applicant: NOVA MEASURING INSTRUMENTS LTD., Rehovot (IL)

(72) Inventors: Danny Grossman, Herzliya (IL); Guy Selickter, Tel Aviv (IL)

(73) Assignee: NOVA MEASURING INSTRUMENTS LTD., Rehovot (IL)

( * ) Notice: Subject to any disclaimer, the term of this patent is extended or adjusted under 35 U.S.C. 154(b) by 0 days.

(21) Appl. No.: 14/785,896

(22) PCT Filed: Apr. 22, 2014

(86) PCT No.: PCT/IB2014/060906
§ 371 (c)(1),
(2) Date: Oct. 21, 2015

(87) PCT Pub. No.: WO2014/174438
PCT Pub. Date: Oct. 30, 2014

(65) Prior Publication Data
US 2016/0084773 A1 Mar. 24, 2016

Related U.S. Application Data
(60) Provisional application No. 61/814,283, filed on Apr. 21, 2013.

(51) Int. Cl.
*G01N 21/00* (2006.01)
*G01N 21/88* (2006.01)
*G01N 21/956* (2006.01)
(52) U.S. Cl.
CPC ........ *G01N 21/8806* (2013.01); *G01N 21/956* (2013.01); *G01N 2021/8848* (2013.01)

(58) Field of Classification Search
CPC ............. G01N 21/9501; G01N 21/94; G01N 21/8806; G01N 21/956; G01N 21/95607
USPC ....................................................... 356/237.2
See application file for complete search history.

(56) References Cited

U.S. PATENT DOCUMENTS

| | | | |
|---|---|---|---|
| 7,050,162 B2 | 5/2006 | Opsal et al. | |
| 7,408,176 B2 * | 8/2008 | Goodwin | G01N 15/1475 250/458.1 |
| 7,961,306 B2 | 6/2011 | Li et al. | |

(Continued)

OTHER PUBLICATIONS

International Search Report, dated Aug. 17, 2014, in corresponding PCT International application No. PCT/IB2014/060906.

*Primary Examiner* — Tarifur Chowdhury
*Assistant Examiner* — MD M Rahman
(74) *Attorney, Agent, or Firm* — Browdy and Neimark, PLLC

(57) ABSTRACT

A control system and method are provided for use in managing optical measurements on target structures. The control system comprises: data input utility for receiving input data indicative of a size of a target structure to be measured and input data indicative of illumination and collection channels of an optical measurement system; data processing utility for analyzing the input data, and an interplay of Point Spread Functions (PSFs) of the illumination and collection channels, and determining data indicative of optimal tailoring of apertures to be used in the optical measurement system for optimizing ensquared energy for measurements on the given target structure, the optimal tailoring comprising at least one of the following: an optimal ratio between numerical apertures of the illumination and collection channels; and an optimal orientation offset of physical apertures in the illumination and collection channels.

14 Claims, 3 Drawing Sheets

(56) References Cited

U.S. PATENT DOCUMENTS

| | | | | |
|---|---|---|---|---|
| 8,681,413 B2* | 3/2014 | Manassen | ............ | G01J 1/4257 359/237 |
| 9,228,943 B2* | 1/2016 | Wang | ..................... | G01N 21/55 |
| 2002/0176081 A1 | 11/2002 | Opsal et al. | | |
| 2014/0015935 A1* | 1/2014 | Piestun | ................. | G06T 7/0048 348/46 |
| 2015/0345934 A1* | 12/2015 | Shafir | .................. | G01N 21/956 356/364 |

* cited by examiner

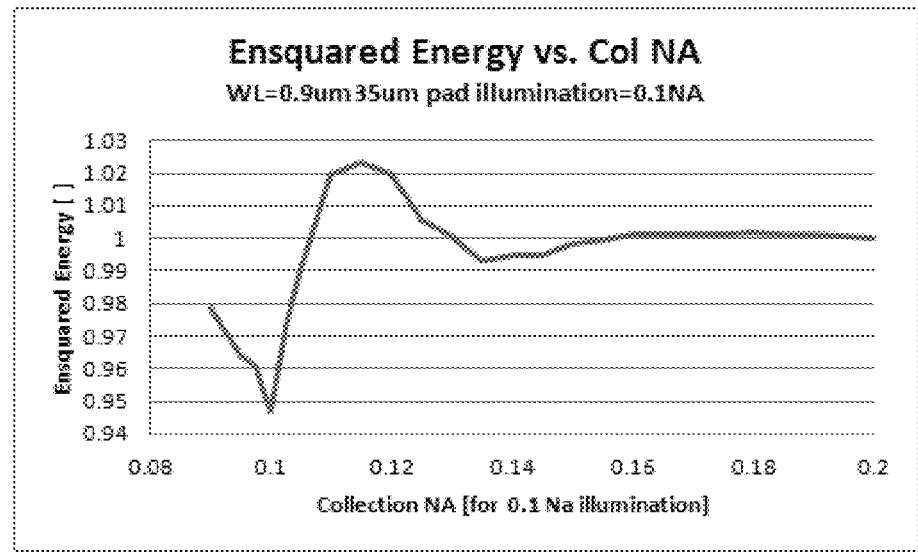
FIG. 2
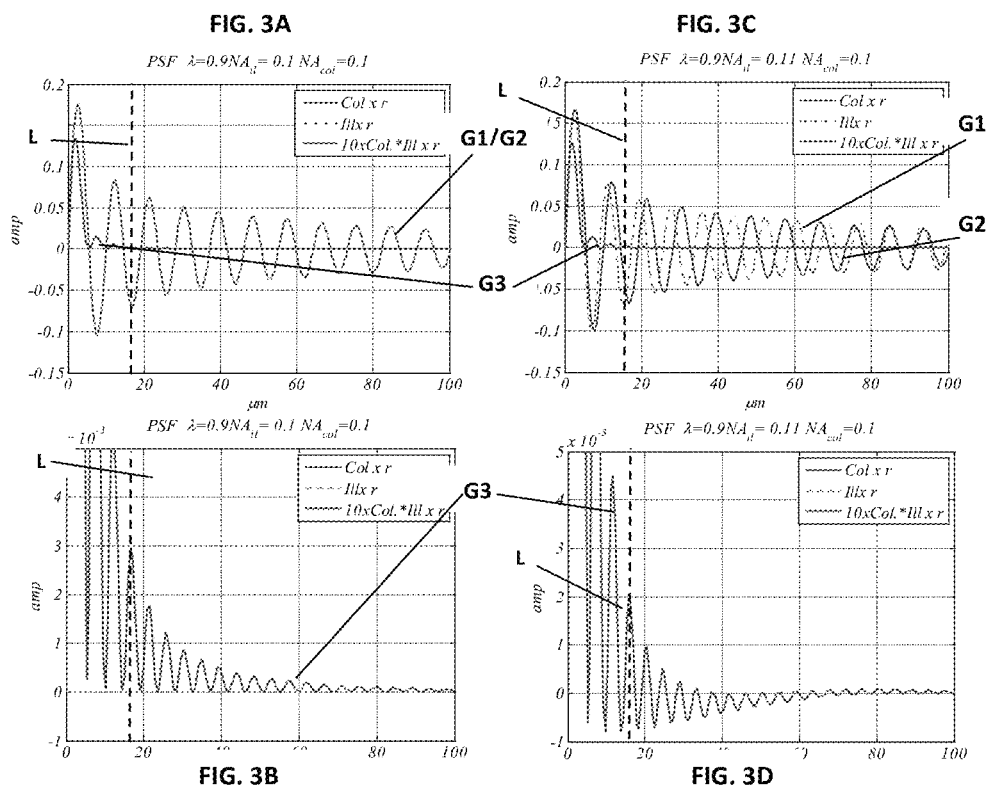

FIG. 4A
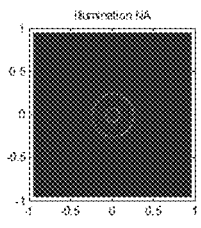
FIG. 4B
FIG. 4C
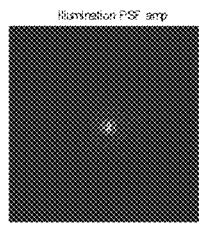
FIG. 4D
FIG. 4E
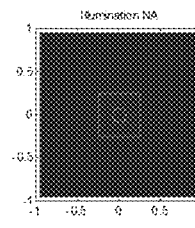
FIG. 4F
FIG. 4G
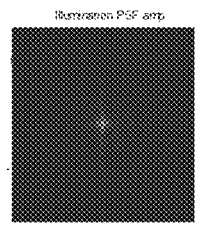
FIG. 4H
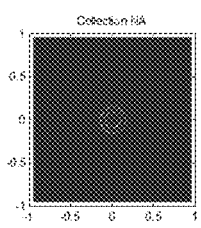
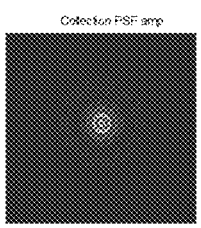
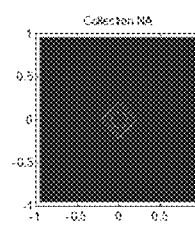
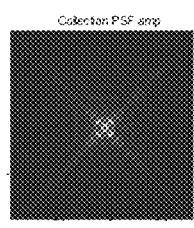

METHOD AND SYSTEM FOR IMPROVING OPTICAL MEASUREMENTS ON SMALL TARGETS

TECHNOLOGICAL FIELD AND BACKGROUND

The present invention is generally in the field of optical measurements on samples, and relates to a method and system for optimizing such optical measurements.

In optical systems (imaging or non imaging), it is important is some cases to collect light from a structure of finite size. To this end, it is desirable to minimize the amount of light that is collected from outside of the structure of interest. Light collected from a measured target by an optical system can be described as ensquared energy associated with the optical system. Maximizing the percent of ensquared energy is sometimes a design optimization target.

GENERAL DESCRIPTION

There is a need in the art for a novel approach for optimizing an optical measurement technique. As indicated above, in various applications, the ensquared energy is to be maximized to provide effective collection of light from a target, especially when measuring on small targets.

The present invention provides an optimization technique based on determining an optimal ratio between numerical apertures (NAs) of collection and illumination channels, and/or optimal shapes (size and geometry) of illumination- and collection-channel apertures, for a given target size, for achieving optimal confinement of the total light collected from the target of finite geometric size into a detector.

For a simple optical system, it is usual to have the collection and illumination channels with the same angular extend or numerical aperture. In general, increasing the numerical aperture reduces the width of point spread function (PSF) of each channel, and this is known to increase optical imaging resolution of the system. The effect on resolution, as described by the size of a diffraction limited spot, is very pronounced: increasing the numerical aperture of collection and illumination by a factor 2× improves resolution by the same factor of 2×. As for reducing ensquared energy, increasing the numerical aperture will have a very marginal effect on ensquared energy. This is shown in Table 1. Here, a diffraction limited optical system is calculated at a wavelength of 0.9 µm, for a pad-like target of a size of 50 µm.

| NA | | |
|---|---|---|
| Illumination | Collection | EE [ ] |
| 0.1 | 0.1 | 0.95 |
| 0.15 | 0.15 | 0.967 |
| 0.2 | 0.2 | 0.97 |
| 0.25 | 0.25 | 0.98 |

It is clear from Table 1 that even increasing the numerical aperture of both the collection and illumination by 2.5× yields negligible benefit in ensquared energy.

In some cases or systems, it is desirable to avoid increase of the numerical aperture, due to various reasons such as cost, durability, aberrations, or complexity. For some systems that might involve modeling or any calculation related to the angular extent, it is desired to keep numerical aperture as small as possible. For the above reasons, the known optical systems are designed to keep the numerical aperture of one of the illumination and collection channels at the desired size, and to increase the numerical aperture of the other channel.

Table 2 shows the results of increasing the numerical aperture of illumination while keeping the numerical aperture of collection channel constant and small.

| NA | | |
|---|---|---|
| Illumination | Collection | EE [%] |
| 0.1 | 0.1 | 0.95 |
| 0.15 | 0.1 | 0.98 |
| 0.2 | 0.1 | 0.99 |
| 0.25 | 0.1 | 0.98 |

It is clear from Table 2 that this approach seems initially better, but the results are not monotonous and the ensquared energy never in fact reaches close to 100%.

Another approach to improving ensquared energy is apodization of collection and or illumination channels. This approach reduces the long tails of either one of illumination and collection PSFs and is effective increasing ensquared energy. The large disadvantage of apodization is the large decrease in transmission associated with it.

The present invention provides a novel approach for optimizing (maximizing) the ensquared energy of an optical system by analyzing the interplay of the collection and illumination PSFs.

The inventors have shown that there is no need to significantly increase the numerical aperture of one of the illumination and collection channels as compared to the other, or in other words, there is no need for significantly increasing a ratio between them, in order to achieve ensquared energy close to 100%. There is also no need to lose significant percentage of power resulting from aggressive apodization.

The inventors have shown that, contrary to the conventional approach of introducing large numerical aperture in either one of collection and illumination channels, using a small difference in these numerical apertures and/or using predetermined different cross-sections of the illuminating and collected beams (i.e. different illumination and collection apertures), yields illumination and collection PSFs that oscillate at slightly different spatial frequencies. The predetermined different illuminating and collection apertures may for example be apertures of a similar shape but oriented such that one is appropriately tilted (rotated) with respect to the other.

Generally speaking, the invention provides the use of tailoring apertures of the illumination and collection, where the effective ensquared energy is actually determined by a relation between the illumination and collection PSF's. The tailoring may be defined by a ratio between the illumination and collection numerical apertures, which according to the invention substantially does not exceed 50%, or may be defined by an orientation offset between the illumination and collection apertures.

As indicated above, the illumination and collection PSFs of slightly different numerical apertures oscillate at slightly different spatial frequencies, and since collected optical field is a result of multiplication of both PSFs of the illumination and collection, coherent summation occurs in the collection channel that gradually develops a phase difference. In this connection, it should be understood that an effect of coherent summation in this case is strictly true for all coherent, incoherent and partially coherent optical systems with illumination and collection channels. When this phase builds up to be close to π, the phase difference approximately nulls out the collected power from this area on the sample. The phase difference is directly related to the relation between the apertures of the illumination and collection channels, i.e. a ratio between the values of the illumination and collection numerical apertures and/or a relative orientation between the physical apertures (orientation offset).

Thus, according to the invention, the optical system, namely its illumination and collection channels are configured to provide an optimal numerical aperture ratio or relation, for a given (e.g. selected) size and geometry of a target, to eliminate or at least significantly reduce detection of light originated from outside of the measured target, and thus maximize the ensquared energy of the optical system.

The present invention provides for optimizing the performance of an optical system by optimizing the multiplication function of the illumination and collection PSFs and/or providing geometric separation of the tails of the illumination and collection PSFs, thereby optimizing the confinement of collected light from a finite sample.

Defining $PSF_{col}$ and $PSF_{ill}$ as the point spread functions (PSFs) of the collection and illumination optical channels respectively, it is known that for a point source and point detector, the light collected from an infinite sample is:

$$e = \int PSF_{ill} \cdot PSF_{col} \, ds$$

The integral is over the entire plane of the sample. It should be noted that the integral is a coherent summation operator of collection and illumination point sources.

The light collected from the test structure or pad is defined by:

$$e_{pad} = \int_{S \in pad} P_{ill} \cdot P_{col} \cdot ds$$

where the integral is calculated over the area defined by the test structure.

The ensquared energy is simply a ratio of the above quantaties squared:

$$E.E = \frac{\|e_{pad}\|^2}{\|e\|^2}$$

In systems having non point sources and detectors, the above is performed for each pair of point source and detector, and the squared quantaties are averaged:

$$E.E_{Extended} = \frac{E_{i,j} \|e_{pad}^{i,j}\|^2}{\sum_{i,j} \|e^{i,j}\|^2}$$

where the summation is over all pairs of point sources and detectors (i,j). The relation between PSF and numerical aperture is given, for an abbetation free system in the focus plane as the Fourier transform of the numerical aperture. Specifically, for a round aperture, the PSF is the well known Arie disk:

$$PSF(r) \sim \frac{J_1(k \cdot NA \cdot r)}{k \cdot NA \cdot r}$$

Here k is the light wave number, NA is the numerical aperture and r is the radius. Away from the center, this function oscilates around zero with a frequency directly related to k·NA.

It should be stated that the above example for a diffraction limited system is not a limitation for the approach and is given as a simple and explicit example. For an aberrated optical system, the transformation between the NA plane and PSF still exists, and the optimization performed should include aberration effects when these are dominant in the PSF behavior.

Thus, according to one aspect of the invention, there is provided a method for use in optical measurements on target structures, the method comprising: receiving and analyzing input data indicative of a size of the target structure to be measured and input data indicative of illumination and collection channels of an optical measurement system, and generating data indicative of optimal tailoring apertures of the illumination and collection to be used in the optical system for maximizing ensquared energy of the optical system for measurements on a given target structure, the optimal tailoring comprising at least one of the following: an optimal ratio between numerical apertures of the illumination and collection channels; and an optimal orientation offset of physical apertures in the illumination and collection channels.

The analysis of the input data comprises analyzing an interplay of Point Spread Functions (PSFs) of the illumination and collection channels. The optimal tailoring provides at least one of the following: the optimal ratio between the illumination and collection numerical apertures substantially not exceeding 50% determined by optimized multiplication function of PSFs of the illumination and collection channels; the optimal orientation offset of apertures in the illumination and collection channels determined by geometric separation of tails of PSFs of the illumination and collection channels, thereby optimizing confinement of collected light from the target structure of the given size.

According to another aspect of the invention, there is provided a control system for use in managing optical measurements on target structures. The control system comprises:

data input utility for receiving input data indicative of a size of a target structure to be measured and input data indicative of illumination and collection channels of an optical measurement system, data processing utility for analyzing the input data, and an interplay of Point Spread Functions (PSFs) of the illumination and collection channels, and determining an optimal tailoring apertures to be used in the illumination and collection channels of the optical measurement system for optimizing ensquared energy for measurements on the given target structure, the optimal tailoring comprising at least one of the following: an optimal ratio between numerical apertures of the illumination and collection channels; and an optimal orientation offset of apertures in the illumination and collection channels.

The control system may further comprise a controller configured and operable for receiving data indicative of the optimal tailoring of the illumination and collection apertures and generating operational data to the optical measurement system for carrying out at least one of the following: controllably varying the numerical aperture of one or both of the illumination and collection channels; and controllably varying orientation of either one of illumination and collection apertures relative to the other.

According to yet another aspect, the invention provides an optical measurement system for measurements on target structures comprising:

an illumination unit defining an illumination channel and comprising a light directing system for directing illuminating light onto the target structure;

a detection unit defining a collection channel and comprising a light collecting system for collecting light returned from the illuminated target structure and directing the collected light to a light detector; and a control unit configured and operable for operating either one or both of the light directing and light collecting systems, for maximizing ensquared energy of the optical system for measurements on a given target structure determined by an optimal relation between Point Spread Functions (PSFs) of the illumination and collection channels, said operating comprising carrying out at least one of the following: controllably varying numerical aperture of one or both of the illumination and collection channels to provide an optimal ratio between them substantially not exceeding 50%; and controllably varying orientation of either one of illumination and collection apertures relative to the other to provide an optimal orientation offset between them.

BRIEF DESCRIPTION OF THE DRAWINGS

In order to better understand the subject matter that is disclosed herein and to exemplify how it may be carried out in practice, embodiments will now be described, by way of non-limiting examples only, with reference to the accompanying drawings, in which:

FIG. 2 exemplifies ensquared energy of the optical system as a function of the numerical aperture of a collection channel, for a given target and given illumination aperture;

FIGS. 3A to 3D exemplify various parameters characterizing the operation of an optical system and demonstrating the principles of the invention for optimizing the numerical apertures of the optical system determined by optimization of a ratio between the numerical apertures of illumination and collection: FIG. 3A shows the PSF behavior in the optical system utilizing the same numerical aperture of the illumination and connection channels of $NA_1=NA_2=0.1$; FIG. 3B shows a zoom in on the multiplication of the PSF; FIGS. 3C and 3D illustrate similar analysis with illumination $NA_1$ of 0.1 and collection $NA_2$ of 0.11;

FIGS. 4A to 4H show another example demonstrating the principles of the invention for optimization ensquared energy based on optimizing a relation between illumination and collection apertures (i.e. cross sections of the illuminating and collected beams): FIGS. 4A-4D show the simulation results for standard circular apertures with 0.96 ensquared energy, and FIGS. 4E-4H show similar simulations for tilted (angular shift) square configurations, yielding 0.995 ensquared energy.

DETAILED DESCRIPTION OF EMBODIMENTS

Figure 1:
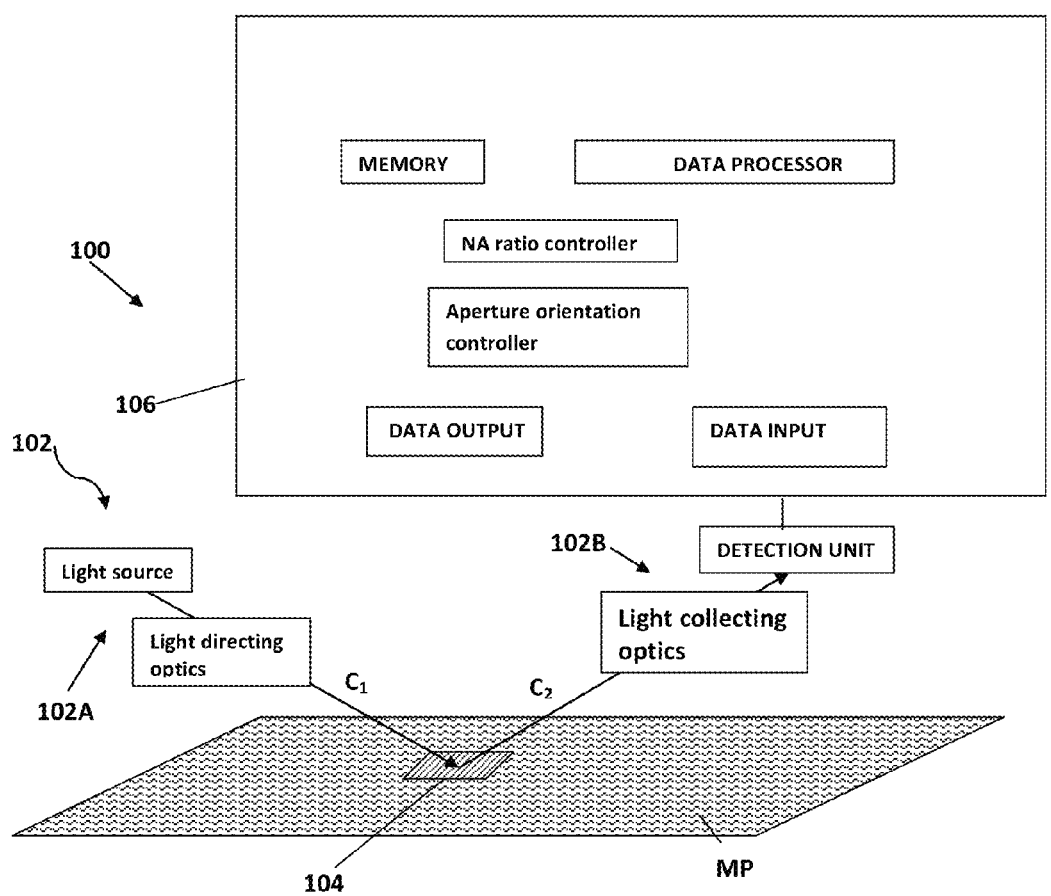
FIG. 1 is a block diagram of an optical system associated with a control system of the invention for optimizing the performance of the optical system.

The present invention is aimed at optimizing optical measurements of features/parameters of small targets, e.g. in patterned structures. In some applications, for example measurements on patterned structures such as semiconductor wafers, a target may be a located in a test site and configured in accordance with the operative (e.g. patterned) region of the structure.

Reference is made to FIG. 1 illustrating schematically a measurement system 100 suitable for using the technique of the invention. The measurement system 100 includes an optical system 102 appropriately accommodated with respect to a measurement plane MP where a test structure (target) 104 is located; and a control unit 106 in communication (via wires or wireless signal transmission) with the optical system 102.

The optical system 102 includes an illumination unit 102A and a detection unit 102B. The illumination unit 102A includes a light source with its associated light directing assembly 104A; and the detection unit 102B includes a detector with its associated light collecting assembly 104B. The light directing/collecting assembly may include one or more apertures (e.g. lenses), as well as any other suitable optical elements providing desired parameters/conditions of light propagation through the system. The illumination unit 102A and the detection unit 102B define, respectively, an illumination channel $C_1$ for focusing an illuminating light onto a measurement spot on the target plane with a numerical aperture $NA_1$, and a collection channel $C_2$ for collecting light from the measurement spot onto a detection plane with a numerical aperture $NA_2$. The illumination channel is configured such that the configuration of the measurement spot corresponds to the shape and size of the target The control unit 106 is typically an electronic device including inter alia such software/hardware utilities/modules as data input (or data readout) and output 106A/106B, memory 106C, and data processor 106D. The control unit 106 may also include one or more controller utilities for controllably adjusting/varying an effective aperture of the optical system. As exemplified in the figure, such one or more controller utilities may include a numerical aperture controller 106E for controllably varying either one or both of the illumination and collection numerical apertures $NA_1$ and $NA_2$ to provide a desired ratio between them; and/or may include aperture orientation controller 106F for controllably adjusting/varying a position and/or shape of either one or both apertures in the illumination and collection channels to provide a desired relative orientation thereof (orientation offset).

The control unit 106 may be configured and operable to receive and analyze input data indicative of the configuration (size and shape) of the target to be measured, as well as other measurement conditions (e.g. given illumination conditions; given (required) illumination or collection aperture) and generate data indicative of the optimal effective numerical apertures of the illumination and collection to be used in the measurements.

For example, as will be exemplified further below, the control unit can analyze the given illumination-channel numerical aperture to be used and/or the shape and size of the physical aperture in the illumination channel, and generate data about corresponding parameters of the collection channel. This data may be provided to the either one or both of the controllers 106E and 106F to operate the optical system accordingly. For example, the system may utilize a set of apertures, for selecting the optimal one, or an aperture of variable shape/size and the operating signal from the controller is used to optimally adjust the shape and size of the aperture of the respective one or both of the illumination and collection channels. Thus, the control unit may be configured for controlling the numerical aperture ratio $R=NA_1/NA_2$ and/or a relative orientations and shapes of the apertures in the illumination and collection channels to provide a desired size of the measurement spot MS required for a given size and geometry of the test structure and a desired relation between the measurement and collection spots.

Further, the control unit may be configured for receiving and processing measured data from the detector for determining one or more conditions/parameters of the structure under measurements.

It should be understood that the illustration in FIG. 1 is schematic and does not limit the invention to any specific configuration of the optical system. The invention may be used in an optical system utilizing oblique or normal incidence mode, as well as optical system operating with either dark- or bright-field mode or both of them; and as indicated above the optical system may be configured for collecting light of a specific polarization state.

In other words, the present invention can optimize (maximize) the ensquared energy of an optical system with any configuration of the illumination and collection channels, by optimizing the effective numerical aperture of the system taking into account the size and geometry of the target, and thus optimizing the interplay of the collection and illumination PSFs.

Reference is made to FIG. 2 showing an example of optimizing the phase difference for a specific optical system. This figure shows a graph of the ensquared energy as a function of the numerical aperture of the collection channel, while keeping the numerical aperture of the illumination channel unchanged, for the measured target in the form of a pad (rectangular geometry) of 0.9 μm×35 μm dimensions. It can be seen that ensquared energy of ~1 can be attained for a constant illumination $NA_1$ of 0.1 and a collection $NA_2$ of 0.107, and also collection $NA_2$ of 0.16 and higher. It should thus be understood that complexity, cost, calculation efforts, etc. can be significantly improved with the selection of the collection numerical aperture $NA_2$ lower than 0.107. It is also instructive to observe the ensquared energy is increased even for reducing the $NA_2$ (in this example, reducing collection $NA_2$ to 0.09 improves the ensquared energy from 95 to 98%). This effect is substantially different than increasing the collection numerical aperture due to simple diffraction first order principles as used in the conventional systems.

The principles of the technique of the present invention, or the physical effect on which the optimization is based, is associated with the coherent summation of the signal due to PSF multiplication.

Reference is made to FIGS. 3A to 3D. FIG. 3A shows the PSF behavior in the optical system utilizing the same numerical aperture of the illumination and connection channels of $NA_1=NA_2=0.1$. The PSFs of the illumination and collection channels in this example are actually identical and therefore are presented by the same graph G1/G2. Also shown in FIG. 3A is their multiplication (graph G3). The PSFs are positive and negative, and display the typical diffraction solution of a Bessel function. The collected power in the detector is the square amplitude of the summation of the PSF multiplication across the entire object plane. FIG. 3B shows a zoom in on the multiplication of the PSF. Since the area differential is proportional to r, the radius, the graphs are multiplied by r.

It will be appreciated that the multiplication yields a function that is positive in every point across the object plane. This means that when the PSF multiplication extends out of the pad (vertical line L at 17.5 um), the detector will collect light from outside the pad. Since the PSF multiplication is positive and the sum is coherent, no destructive interference occurs and energy can be collected efficiently from outside the pad.

In contrast, FIGS. 3C and 3D illustrate similar analysis with illumination $NA_1$ of 0.1 and collection $NA_2$ of 0.11. It will be appreciated that the multiplication of both PSF yields a function that starts in initial point as positive ("in phase"), but due to different periods between the multiplied PSF, a gradual phase builds up between the two PSFs, resulting in oscillations from negative to positive values (FIG. 3D). When summing over the entire object field, these areas are canceled out do to the contribution of positive and negative values, and contribute very little to the overall results. Thus, the out of pad energy to the detector is "nulled out" and ensquared energy can easily be increased with very little increase in the numerical aperture of collection (and even decrease of the numerical aperture, as described above).

This optimization can be used to optimize the system to any confined energy specification of arbitrary shape, across single, several, multiple wavelengths.

Reference is now made to FIGS. 4A to 4H showing another example further illustrating the above described principles of the invention. In this example, optimization of ensquared energy is demonstrated based on the principle of geometric separation of the PSF tails that optimizes the confinement of collected light. FIGS. 4A-4D show the simulation results for standard circular apertures with 0.96 ensquared energy, and FIGS. 4E-4H show similar simulations for tilted (angular shift) square configurations, yielding 0.995 ensquared energy.

More specifically, FIGS. 4A and 4B show the configuration of apertures in the illumination and collection, which are round apertures with central obscuration (the obscuration might be a result of using reflective optics), and FIGS. 4C and 4D show the corresponding illumination- and collection-channel PSFs. The resultant ensquared energy for a particular pad (target) size and wavelength is 0.96.

FIGS. 4E-4H exemplify a specific tilted square configuration of the aperture, designed to minimize the overlap of the long tails of the PSF function of the collection and illumination. More specifically, FIGS. 4E and 4F show the apertures' configurations in the illumination and collection channels, and FIGS. 4G and 4H show the corresponding illumination- and collection-channel PSFs.

Comparing the PSF function obtained with the round and square apertures, it is seen that while the round aperture seems to decrease the intensity of light in the tails of the PSF function of each of the collection and illumination separately (with respect to the square aperture), the multiplication of the illumination and collection is much smaller in the tails in the tilted square aperture since the high intensity tails do not overlap geometrically. This leads to 0.995 ensquared energy for the square aperture configuration using tilt between collection and illumination square apertures. The optimization of each PSF separately as considered in the conventional approach, leads to much inferior solution as compared to the optimization of the multiplication of both collection and illumination PSFs.

The above is a specific but not limiting example of the principle of the present invention using shapes of the apertures, numerical aperture differences to minimize the multiplication function of the illumination and collection PSFs and thus to optimize the optical power confinement in an optical system.

The invention claimed is:
1. A control system for use in managing optical measurements on target structures, the control system comprising:
   data input utility for receiving input data indicative of a size of a target structure to be measured and input data indicative of illumination and collection channels of an optical measurement system, data processing utility for analyzing the input data, and an interplay of Point Spread Functions (PSFs) of the illumination and collection channels, and determining data indicative of optimal tailoring apertures to be used in the optical measurement system for optimizing ensquared energy for measurements on the given target structure, the optimal tailoring comprising determining an optimal orientation offset of physical apertures in the illumination and collection channels determined by geometric separation of tails of PSFs of the illumination and collection channels, providing an optimal ratio between numerical apertures of the illumination and collection channels substantially not exceeding 50% determined by optimized multiplication function of PSFs of the illumination and collection channels, optimizing confinement of collected light from the target structure of the given size.

2. The control system of claim 1, further comprising a controller configured and operable for receiving data indicative of the optimal tailoring and generating operational data to the optical measurement system for carrying out at least one of the following: controllably varying the numerical aperture of one or both of the illumination and collection channels; and controllably varying orientation of either one of illumination and collection apertures relative to the other.

3. The control system of claim 1, wherein said optimal tailoring provides a desirably small difference in the numerical apertures of the illumination and collection channels and the predetermined orientation offset of the illumination and collection apertures, yielding illumination and collection PSFs that oscillate at slightly different spatial frequencies, thereby significantly reducing detection of light originated from outside of the measured target.

4. An optical measurement system for measurements on target structures, the system comprising: an illumination unit defining an illumination channel and comprising a light directing system for directing illuminating light onto the target structure; a detection unit defining a collection channel and comprising a light collecting system for collecting light returned from the illuminated target structure and directing the collected light to a light detector; and the control system of claim 1.

5. An optical measurement system for measurements on target structures, the system comprising:
an illumination unit defining an illumination channel and comprising a light directing system for directing illuminating light onto the target structure;
a detection unit defining a collection channel and comprising a light collecting system for collecting light returned from the illuminated target structure and directing the collected light to a light detector;
wherein said illumination and detection units are characterized by the following: orientation of either one of illumination and collection apertures relative to the other is selected to provide an optimal orientation offset between the illumination and collection apertures determined by geometric separation of tails of Point Spread Functions (PSFs) of the illumination and collection channels, providing an optimal ratio between the numerical apertures of the illumination and collection channels determined for maximizing ensquared energy of the system for measurements on a given target structure, said optimal ratio substantially not exceeding 50% determined by optimized multiplication function of PSFs of the illumination and collection channels.

6. The optical measurement system of claim 5, wherein said optimal ratio and said optimal orientation offset provide a desirably small difference in the numerical apertures of the illumination and collection channels and the predetermined orientation offset of the illumination and collection apertures, yielding illumination and collection PSFs that oscillate at slightly different spatial frequencies, thereby significantly reducing detection of light originated from outside of the measured target.

7. The system of claim 5, wherein said illumination and detection channels are configured for oblique or normal incidence mode.

8. The system of claim 5, wherein the illumination and detection units are configured operation with at least one of dark- and bright-field modes.

9. The system of claim 5 configured for collecting light of a specific polarization state.

10. An optical measurement system for measurements on target structures, the system comprising:
an illumination unit defining an illumination channel and comprising a light directing system for directing illuminating light onto the target structure;
a detection unit defining a collection channel and comprising a light collecting system for collecting light returned from the illuminated target structure and directing the collected light to a light detector; and
a control unit configured and operable for operating either one or both of the light directing and light collecting systems, for maximizing ensquared energy of the optical system for measurements on a given target structure, said operating comprising: controllably varying orientation of either one of illumination and collection apertures relative to the other to provide an optimal orientation offset between them determined by geometric separation of tails of Point Spread Functions (PSFs) of the illumination and collection channels, thereby controllably varying numerical aperture of one or both of the illumination and collection channels to provide an optimal ratio between them substantially not exceeding 50% determined by optimized multiplication function of PSFs of the illumination and collection channels.

11. The optical measurement system of claim 10, wherein said optimal tailoring provides a desirably small difference in the numerical apertures of the illumination and collection channels and the predetermined orientation offset of the illumination and collection apertures, yielding illumination and collection PSFs that oscillate at slightly different spatial frequencies, thereby significantly reducing detection of light originated from outside of the measured target.

12. A method for use in optical measurements on target structures, the method comprising:
receiving and analyzing input data indicative of a size of the target structure to be measured and input data indicative of illumination and collection channels of an optical measurement system, and
generating data indicative of optimal tailoring apertures to be used in the optical system for maximizing ensquared energy of the optical system for measurements on a given target structure, the optimal tailoring comprising: providing optimal orientation offset of apertures in the illumination and collection channels determined by geometric separation of tails of Point Spread Functions (PSFs) of the illumination and collection channels thereby providing an optimal ratio between numerical apertures of the illumination and collection channels substantially not exceeding 50% determined by optimized multiplication function of PSFs of the illumination and collection channels, optimizing confinement of collected light from the target structure of the given size.

13. The method according to claim 12, wherein said analyzing of the input data comprising of analysis of the interplay of Point Spread Functions (PSFs) of the illumination and collection channels.

14. The method of claim 12, wherein said optimal tailoring provides a desirably small difference in the numerical apertures of the illumination and collection channels and the predetermined orientation offset of the illumination and collection apertures, yielding illumination and collection PSFs that oscillate at slightly different spatial frequencies, thereby significantly reducing detection of light originated from outside of the measured target.

* * * * *